United States Patent [19]

Wilburn

[11] Patent Number: 5,108,754

[45] Date of Patent: Apr. 28, 1992

[54] ORTHOMOLECULAR METHOD OF TREATING SICKLE CELL DISEASE

[76] Inventor: Michael Wilburn, 709 Washington St., Longview, Tex. 75601

[21] Appl. No.: 652,773

[22] Filed: Feb. 8, 1991

[51] Int. Cl.$^5$ .................. A61K 9/08; A61K 9/14; A61K 31/355; A61K 37/02

[52] U.S. Cl. .................. 424/422; 424/423; 424/434; 424/435; 424/451; 424/464; 424/466; 424/489; 514/815; 514/951; 514/953; 514/960; 514/962; 514/966

[58] Field of Search ............... 424/422, 423, 434, 435, 424/436, 451, 464, 489; 514/815, 951, 953, 960, 962, 966

[56] References Cited

U.S. PATENT DOCUMENTS

| | | | |
|---|---|---|---|
| 4,390,526 | 6/1983 | Gorecki et al. | 424/177 |
| 4,866,052 | 9/1989 | Hider et al. | 514/184 |
| 4,983,626 | 1/1991 | Ismail | 514/458 |

OTHER PUBLICATIONS

"A Decrease In Irreversibly Sickled Erythrocytes In Sickle Cell Anemia Patients Given Vitamin E", Natta et al., *American Journal of Clinical Nutr.*, May 1980, 33(5) pp. 468-471.

Batlle et al., "Two Cases of Infantile Porphyria cutanea Tarda: Successful Treatment with Oral S-Adenosyl-L-Methionine and Low-Dose Oral Chloroquine," Brit. J. of Dermatology (1987), vol. 116, pp. 407-413.

Tangney et al., "Selected Indices of Micronutrient Status in Adult Patients With Sickle Cell Anemia (SCA)," *American Journal of Hematology* (1989), vol. 32.

*Primary Examiner*—Thurman K. Page
*Assistant Examiner*—Carlos Azpura
*Attorney, Agent, or Firm*—Roper & Quigg

[57] ABSTRACT

A method for preventing the sickling of sickle cells in a patient having sickle cell disease, the method which comprises administering to the patient a therapeutically effective amount of a compound having the formula:

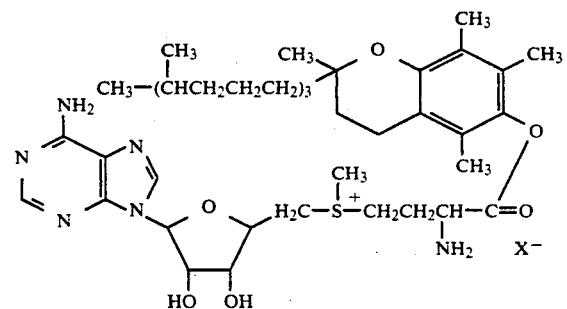

wherein X$^-$ is selected from the group consisting of iodide, chloride, bromide, hydroxyl, nitrite, phosphate and acetate.

13 Claims, No Drawings

ORTHOMOLECULAR METHOD OF TREATING SICKLE CELL DISEASE

BACKGROUND OF THE INVENTION

1. Field of the Invention

The present invention relates to novel compounds and pharmaceutical preparations including the same which are useful in the treatment of sickle cell disease.

2. Description of the Prior Art

Sickle cell disease is caused by a hemoglobin mutant called hemoglobin S, known as HbS. The mutation of HbS involves the replacement of a polar residue, glutamic acid, by a hydrophobic one, valine, in the 6th position of the β-chains, and this renders the HbS capable of polymerization in the deoxygenated form. See Pauling et al., Science 110, 543 (1949); Ingram: Nature, (London) 178, 792 (1956). In the deoxygenated state, the HbS molecules aggregate in the form of elongated microtubular structures which distort the shape of the red cell to a sickle shape. The sickled cells tend to block the blood capillaries and ultimately give rise to the sequelae of sickle cell disease.

There are known compounds which affect polymerization of HbS, and there is a clear distinction between those which are antisickling agents and those which are antigelling agents.

The antisickling agents are those which are able to pass through the cell membrane of the erythrocytes and prevent or reverse sickling; the antigelling agents are those which are adapted to prevent polymerization of deoxygenated HbS, but which do not pass through the cell membrane in sufficient quantities and thus are not adapted to prevent or reverse sickling when contacted with red blood cells of a patient suffering from sickle cell disease.

Antigelling agents are not capable of preventing sickling, nor are they adapted to reverse sickling when incubated with erythrocytes.

In this regard, Tables II and III of U.S. Pat. No. 4,390,526 disclose various antisickling and antigelling agents, respectively, which have been developed in prior efforts to alleviate the deleterious effects of sickle cell disease. Known antisickling agents disclosed therein include DL-glyceraldehyde, various aldehydes and ketones, alkyl urea and urea, 2(benzoyl amino) pyridinium benzoate, dibromo aspirin, 3,4-dihydro-2,2-dimethyl 2H-1 benzopyridinium-6-butyric acid, pyridoxal, cystamine, nitrogen mustard, potassium cyanate, dimethyl adipimidate, and benzyl esters of certain amino acids. Cited antigelling agents include tri- and tetrapeptides, aromatic compounds, aromatic amino acids and peptides, and oligopeptides.

Sickle cell disease has been studied extensively, but in spite of this there does not exist a universally acceptable therapeutic agent for the treatment of this disease. During recent years attempts have been made to provide such agents. Some of these efforts are based on the use of three types of compounds:

a. Agents which bind covalently with the hemoglobin molecule;

b. Agents which bind non-covalently to this molecule; and c. Agents affecting the cell membrane.

A number of known antisickling agents have a rather high toxicity, one of these being, for example, potassium cyanate. Moreover, it is generally agreed that none of the known agents for treating sickle cell anemia provide satisfactorily efficacious results over prolonged periods of time.

It would therefore be highly desirable to provide an active agent which is effective in preventing the sickling of erythrocytes in sickle cell patients, without the accompanying toxicity that is characteristic of many prior art treating agents.

SUMMARY OF THE INVENTION

According to the present invention, a pharmaceutical composition for preventing the sickling of sickle cells in a patient having sickle cell disease is provided. The composition comprises a pharmaceutically acceptable carrier and a therapeutically effective amount of an active agent having the formula:

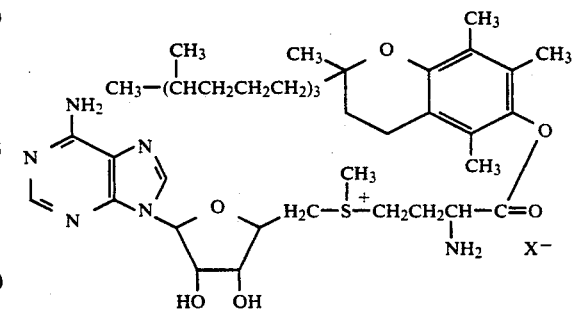

wherein $X^-$ is selected from the group consisting of iodide, chloride, bromide, hydroxyl, nitrite, phosphate and acetate. A preferred compound is provided where $X^-$ comprises iodide.

The pharmaceutical compositions provided by the instant invention employ a therapeutically effective amount of the above-indicated active agent. This amount will generally comprise about 10 mg to about 1200 mg of the active agent per kilogram of patient body weight per day.

The novel compounds provided by the invention are highly viscous substances which are preferably provided in a suitable pharmaceutically acceptable carrier well-known in the art, in either solid or liquid forms. Exemplary solid form preparations include powders, tablets, dispersible granules, capsules, cachets and suppositories. Suitable liquid forms for delivering the compositions of the invention include solutions, suspensions and emulsions.

The pharmaceutical compositions of the invention may include one or more additional ingredients well-known in the art selected from the group consisting of diluents, flavoring agents, solubilizing agents, colorants, lubricants, suspending agents, binders, tablet disintegrating agents, stabilizers, buffers, sweeteners, dispersants, thickeners, and mixtures thereof.

The present invention also contemplates a method for preventing the sickling of sickle cells in a patient having sickle cell disease. The method comprises administering to said patient a therapeutically effective amount of a compound having the formula:

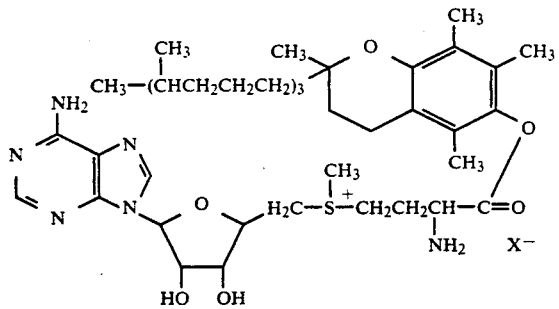

wherein X⁻ is selected from the group consisting of iodide, chloride, bromide, hydroxyl, nitrite, phosphate and acetate.

Administration of the novel compounds of the invention may be performed by well-known techniques including intravenous injection, intramuscular injection, oral administration, topical administration, rectal administration, and inhalation.

The present invention also contemplates a pharmaceutical composition for preventing the sickling of sickle cells in a patient having sickle cell disease which composition comprises an active agent system that includes the novel compound of the invention, together with the protein glutathione, or proteins or peptides containing glutathione, and at least one nutritional agent. This pharmaceutical composition comprises a pharmaceutically acceptable carrier and an active agent system which comprises:

(a) from about 1% to about 98% by weight, based on the total weight of the pharmaceutical composition, of a compound having the formula:

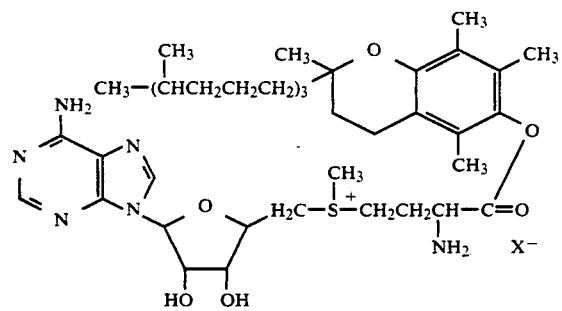

wherein X⁻ is selected from the group consisting of iodide, chloride, bromide, hydroxyl, nitrite, phosphate and acetate;

(b) from about 1% to about 98% by weight, based on the total weight of the pharmaceutical composition, of glutathione, or proteins or peptides containing glutathione; and (c) from about 1% to about 98% by weight, based on the total weight of the pharmaceutical composition, of a nutritional agent selected from the group consisting of vitamin A, vitamin D, vitamin C, vitamin E, folic acid, vitamin $B_1$, vitamin $B_2$, vitamin $B_6$, vitamin $B_{12}$, pantothenic acid, biotin, phosphatidyl choline, molybdenum, selenium, potassium, iron, magnesium, copper, zinc, manganese, chromium, nickel, calcium, phosphorous, iodine, cobalt, and mixtures thereof.

A method for preventing the sickling of sickle cells in a patient having sickle cell disease, by the administration of a therapeutically effective amount of this pharmaceutical composition, is also provided.

DETAILED DESCRIPTION OF THE INVENTION

Before discussing the preferred aspects of the present invention summarized above, it will be useful to provide a clinical overview of sickle cell anemia, as well as the basic laboratory techniques for determining the presence of the disease in an individual.

Sickle cell disease is a hereditary blood disease in which the red blood cells sometimes assume unusual shapes. The word "sickle" was first used in 1910, when Dr. J. B. Herrick, a Chicago physician was examining the blood of an anemic black student from the West Indies. Using microscopic studies, Dr. Herrick observed peculiar elongated sickled shaped cells in the student's blood smear.

Hemoglobin (Hb) is a substance in all red blood cells, regardless of their shape. Hemoglobin gives blood its red color and transports oxygen from the lungs to various parts of the body. Normal hemoglobin is HbA; sickle hemoglobin is HbS. Hemoglobins C, E and A2 are found in persons with thalassemia.

Hemoglobin is a conjugate protein and consists of four polypeptide chains. Each of the polypeptide chains contains a heme-group. Adult hemoglobin (HbA) contains two pairs of chains, alpha and beta chains. Each alpha chain contains 141 amino acids while each beta chain consists of 146 amino acids. Hemoglobin A2 is a second adult hemoglobin containing two alpha and two delta chains. Hemoglobin A2 (HbA2) is found in approximately two percent of normal adults. Abnormal levels of HbA2 can be found in homozygous sickle cell without HbA and in thalassemia.

Fetal hemoglobin (HbF) consists of a pair of alpha and a pair of gamma chains. The key to laboratory differentiation is the resistance of HbF to alkaline denaturization. HbF consists of 80% of the total hemoglobin at birth. By the fourth month after birth only ten percent of HbF will remain.

Abnormal hemoglobin may be a result of some abnormality in the synthesis of a polypeptide chain. Abnormality can take the form of amino acid substitution or inadequate production of normal chains, as in the thalassemias. An example of abnormality through substitution is sickle cell disease. In sickle cell disease, hemoglobin S occurs through the substitution of valine for glutamic acid in the sixth position of the beta chain.

The heterozygote possessing only one gene is said to have sickle trait (HbAS) while the homozygote possessing the two abnormal genes form the severe and often fatal, sickle cell anemia. Hemoglobin C is an abnormal hemoglobin with two alpha and two beta chains. In hemoglobin C, lysine is substituted for glutamic acid in the sixth position. Hemoglobin D consists of two alpha chains and two beta chains. Hemoglobin E (HbE) consists of two alpha chains and two beta chains. In HbE, lysine is substituted for glutamic acid in the twenty-sixth position. Hemoglobin M is characterized by amino acid substitution near the heme group in both chains.

The tendency towards sickling is dependent on both the relative quantity of HbS in the erythrocytes and the level of oxygen tension in the micro environment. Under conditions of low oxygen tension, HbS has a lower solubility than HbA. This causes sickling and other distortions of red blood cells, resulting in pain, elevation of body temperature, anemia, lethargy, infarction of organs, leg ulcers, paralysis and other abnormalities.

Red cells with 100% HbS will sickle at physiological oxygen tension, but with a reduction of the levels of HbS (e.g., with corresponding increases in HbA level), progressively lower levels of oxygen are required to induce sickling.

Abnormal pain is one of the most common symptoms during sickle cell crises. Pain during a crisis may be due to the occlusion of blood vessels by great numbers of sickled red cells. Spleen and liver infection may result in pain. Depending upon the degree of complication in sickle cell disease, the following may be noticed: pain relating to pancreatic problems will cause an elevation of serum lipase and amylase; pain due to kidney problems will cause an elevation in urea nitrogen and creatinine.

Liver involvement may be the cause of intense jaundice that is common in sickle cell disease. Hyperbilirubinemia of greater than 25 mg/dl (50% conjugated) may occur. Aspartate aminotransferase (AST), alanine aminotransferase (ALT), alkaline phosphatase, and glutamyl transferase enzymes (GGT) will be elevated.

Splenic sequestration may cause a decrease in hemoglobin and hematocrit. In normal persons, the spleen contains approximately 20-30 ml of erythrocytes. In splenomegaly the amount may reach many times the normal volumes. The time of transition of erythrocytes through the spleen will be increased. The erythrocytes under these circumstances may be subjected to some lytic effects. This may result in low hemoglobin and hematocrit values and increases in hemolysis. Total serum bilirubins may be increased. Severe anemia may develop.

Stasis causes the metabolic consumption of glucose by the erythrocytes. The glucose consumption increases with hemolysis. Selective destruction of abnormal erythrocytes will be accelerated or increased by splenic pooling. Splenic pooling may be responsible for low platelet counts and massive hemolysis, and hematuria may result. As the erythrocytes pass through the spleen, selective destruction of abnormal cells is called culling. This culling in the spleen may be responsible for the increase in total bilirubin, decrease in hemoglobin and hematocrit values observed in sickle cell patients.

Target cells and nucleated red cells are frequently observed in the peripheral smear of patients with sickle cell disease. Target cells are erythrocytes with an abnormal distribution of hemoglobin. Hemoglobin C disease is characterized by increased numbers of target cells and rod-shaped crystals of hemoglobin C. Reticulocytosis and siderocytes (iron granules) are commonly seen in sickle cell disease.

Factor VIII is significantly increased in all studies regardless of assay. Factors V and XIII are low while fibrinogen levels are relatively normal. Fibrin degradation products are increased in sickle cell disease. Zinc levels in patients with sickle cell disease are low.

Leukocytosis with white blood cell (WBC) counts of 10,000-20,000 mm$^3$ and elevated temperature may be a sign of bacterial sepsis. Bacterial culture of blood, urine, cerebrospinal fluid (CSF) and stool may be helpful in isolating the bacterial agents. Viral cultures for cytomegalo virus (CMV) and Epstein-Bar virus (EBV) may be helpful. Meningitis and septicemia are common in sickle cell disease. The majority of bacterial infections in sickle cell children are caused by *Streptococcus pneumonia*. Approximately 70-80% of meningitis in sickle cell children is *Pneumococcal meningitis*. *Hemophilus influenzae* is the second most common agent of meningitis in sickle cell children. Staphylococcus, Salmonella and *Escherichia coli* are common isolates in bone problems and ulcers in sickle cell children.

Complete blood count (CBC), including a good peripheral smear for a 100 cell differential count can be of great importance in the diagnosis of some stages of sickle cell disorder. Depending upon the stage and degree of complication, CBC and differential techniques will expose the sickling of red blood cells, decreases in hemoglobin and hematocrit, increases or decreases in reticulocytes, increases in cells with Howell Jolly bodies, nucleated red cells, target cells, siderocytic granules, and altered platelet levels.

Diagnosis of sickle cell anemia may be initiated at birth or during delivery, wherein a cord blood sample from the discarded end of the umbilical cord is tested by hemoglobin electrophoresis to determine the presence of unusual or abnormal hemoglobins. This screening test is followed by another electrophoresis by the fourth month if the initial screen showed some abnormal or unusual hemoglobin. This electrophoretic test at the fourth month will help quantify any unusual or abnormal hemoglobin.

With a standard alkaline buffer (cellulose acetate) electrophoresis technique, hemoglobins S, D, and G all have identical migration rates. Hemoglobin C, E, and O migrate to the same point. To differentiate these hemoglobins and separate them according to their migration rates, electrophoresis in citrate agar at a pH of 6.0 to 6.2 is employed. Citrate agar at pH 6.0-6.2 allows HbS to be distinguished from HbE and HbO. Citrate agar has four major zones, namely HbF, HbA, HbS, and HbC. Hemoglobin F (HbF) is the fastest hemoglobin, moving from cathode to anode. Under standard alkaline buffer hemoglobin electrophoretic conditions, HbA, HbF and Hemoglobin S migrate approximately together but with citrate agar, HbF migrates well ahead of HbS and HbC.

The following screening techniques are useful in identifying prospective patients to be treated according to the present invention.

DEMONSTRATION OF SICKLING BY METABISULFITE METHOD

Dissolve a 200 mg capsule of sodium metabisulfite in 10 milliliters distilled water.

1. Place a drop of oxalate blood on a slide and add 2 drops of freshly prepared sodium metabisulfite solution (2% metabisulfite solution).
2. Mix, cover with coverslip, and allow to stand for 30 minutes. Examine microscopically for sickling. Both sickle cell (HbSS) and sickle cell trait (HbAS) will be positive in individuals having sickle cell anemia.

When reducing substances are not available, a drop of blood may be placed on a glass slide, covered and sealed. Sickling will occur after several hours.

SOLUBILITY TESTS—DITHIONITE

The relative insolubility of deoxygenated HbS has led to the development of many tests. Phosphate buffers, lysine and reducing agents are utilized in these tests. Deoxyhemoglobin S is less soluble than HbA when reduced by dithionite in phosphate buffer solution. The result is a cloudy suspension of protein crystals in the tube with HbS and clear or non-turbid suspension in the tube containing HbA. Both hemoglobin SS and AS are positive.

The following procedure may be followed according to this technique:
1. Pipet 2 ml of reagent (dithionite) into labeled tubes;
2. Add 20 microliter of whole blood, ethylenediaminetetraacetic (EDTA) or heparin;
3. Mix well and let stand for 10 minutes;
4. Read and record the turbidity;
5. Include the positive control.

Opacity indicates an insoluble hemoglobin S.

The need for performing a citrate agar hemoglobin electrophoresis test on any person who tested positive with any of the sickle cell screening tests cannot be over-looked.

Once a patient has been diagnosed as having sickle cell disease using the above-discussed analytical or other acceptable techniques, the individual may be treated with the pharmaceutical composition provided by the present invention in order to prevent the sickling of erythrocytes in the sickle cell patient.

According to one aspect of the invention, a pharmaceutical composition for preventing the sickling of sickle cells in a sickle cell patient is provided. The composition comprises a pharmaceutically acceptable carrier and a therapeutically effective amount of an active agent having the formula:

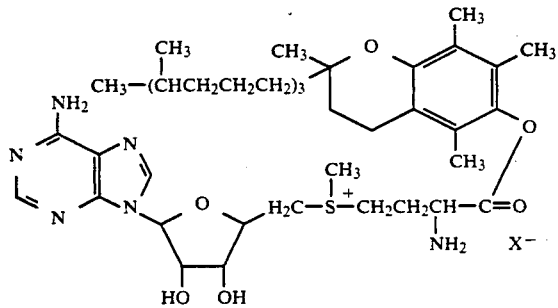

wherein $X^-$ is selected from the group consisting of iodide, chloride, bromide, hydroxyl, nitrite, phosphate and acetate. A preferred compound is provided where $X^-$ is iodide, in which case the compound can be named α-(S-adenosylmethionine)-O-tocopherol.

The novel pharmaceutical compositions of the invention include a therapeutically effective amount of the active agent indicated above. This effective amount will generally comprise from about 10 mg to about 1200 mg of the active agent per kilogram of patient body weight per day. This effective amount can vary depending upon the physical status of the patient and other factors well known in the art. Moreover, it will be understood that this dosage of active agent can be administered in a single or multiple dosage units to provide the desired therapeutic effect. If desired, other therapeutic agents can be employed in conjunction with those provided by the present invention.

The compounds of the invention are preferably delivered to the patient by means of a pharmaceutically acceptable carrier. Such carriers are well known in the art and generally will be in either solid or liquid form. Solid form pharmaceutical preparations which may be prepared according to the present invention include powders, tablets, dispersible granules, capsules, cachets and suppositories. In general, solid form preparations will comprise from about 5% to about 90% by weight of the active agent.

A solid carrier can be one or more substances which may also act as diluents, flavoring agents, solubilizers, lubricants, suspending agents, binders or tablet disintegrating agents; it can also be encapsulating material. In powders, the carrier is a finely divided solid which is in admixture with the viscous active compound. In tablets, the active compound is mixed with a carrier having the necessary binding properties in suitable proportions and compacted to the shape and size desired. Suitable solid carriers include magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating materials as a carrier which may provide a capsule in which the active component (with or without other carriers) is surrounded by carrier, which is thus in association with it. Similarly, cachets are included. Tablets, powders, cachets, and capsules can be used as solid dosage forms suitable for oral administration.

If desired for reasons of convenience or patient acceptance, pharmaceutical tablets prepared according to the invention may be provided in chewable form, using techniques well known in the art.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby to solidify.

Liquid form preparations include solutions, suspensions, and emulsions. As an example may be mentioned water or water/propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizers and thickening agents as desired. Aqueous suspensions suitable for oral use can be made my dispersing the finely divided active component in water with a viscous material, i.e., natural or synthetic gums, resins, methylcellulose, sodium carboxymethylcellulose, and other well known suspending agents.

Liquid pharmaceutical preparations may comprise up to 100% by weight of the subject active agent.

Also contemplated as suitable carriers are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing useful liquid form preparations may be water, isotonic water, ethanol, glycerine, propylene glycol, and the like as well as mixtures thereof. Naturally, the liquid utilized will be chosen with regard to the route of administration. For example, liquid preparations containing large amounts of ethanol are not suitable for parenteral use.

The pharmaceutical preparation may also be in a unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these in packaged form.

The pharmaceutical preparations of the invention may include one or more preservatives well known in the art, such as benzoic acid, sorbic acid, methylparaben, propylparaben and ethylenediaminetetraacetic acid (EDTA). Preservatives are generally present in amounts up to about 1% and preferably from about 0.05 to about 0.5% by weight of the pharmaceutical composition.

Useful buffers for purposes of the invention include citric acid-sodium citrate, phosphoric acid-sodium phosphate, and acetic acid-sodium acetate in amounts up to about 1% and preferably from about 0.05 to about 0.5% by weight of the pharmaceutical composition. Useful suspending agents or thickeners include cellulosics like methylcellulose, carageenans like alginic acid and its derivatives, xanthan gums, gelatin, acacia, and microcrystalline cellulose in amounts up to about 20% and preferably from about 1% to about 15% by weight of the pharmaceutical composition.

Sweeteners which may be employed include those sweeteners, both natural and artificial, well known in the art.

Sweetening agents such as monosaccharides, disaccharides and polysaccharides such as xylose, ribose, glucose, mannose, galactose, fructose, dextrose, sucrose, maltose, partially hydrolyzed starch or corn syrup solids and sugar alcohols such as sorbitol, xylitol, mannitol and mixtures thereof may be utilized in amounts from about 10% to about 60% and preferably from about 20% to about 50% by weight of the pharmaceutical composition. Water soluble artificial sweeteners such as saccharin and saccharin salts such as sodium or calcium, cyclamate salts, acesulfame-K, aspartame and the like and mixtures thereof may be utilized in amounts from about 0.001% to about 5% by weight of the composition.

Flavorants which may be employed in the pharmaceutical products of the invention include both natural and artificial flavors, and mints such as peppermint, menthol, vanilla, artificial vanilla, chocolate, artificial chocolate, cinnamon, various fruit flavors, both individually and mixed, in amounts from about 0.5% to about 5% by weight of the pharmaceutical composition.

Colorants useful in the present invention include pigments which may be incorporated in amounts of up to about 6% by weight of the composition. A preferred pigment, titanium dioxide, may be incorporated in amounts up to about 1%. Also, the colorants may include other dyes suitable for food, drug and cosmetic applications, known as F.D. & C. dyes and the like. Such dyes are generally present in amounts up to about 0.25% and preferably from about 0.05% to about 0.2% by weight of the pharmaceutical composition. A full recitation of all F.D. & C. and D. & C. dyes and their corresponding chemical structures may be found in the *Kirk-Othmer Encyclopedia of Chemical Technology*, in Volume 5, at pages 857-884, which text is accordingly incorporated herein by reference.

Useful solubilizers include alcohol, propylene glycol, polyethylene glycol and the like and may be used to solubilize the flavors. Solubilizing agents are generally present in amounts up to about 10%; preferably from about 2% to about 5% by weight of the pharmaceutical composition.

Lubricating agents which may be used when desired in the instant compositions include silicone oils or fluids such as substituted and unsubstituted polysiloxanes, e.g., dimethyl polysiloxane, also known as dimethicone. Other well known lubricating agents may be employed.

The present invention also contemplates a method for preventing the sickling of sickle cells in a patient having sickle cell disease. The method comprises administering to said patient a therapeutically effective amount of an active agent having the formula:

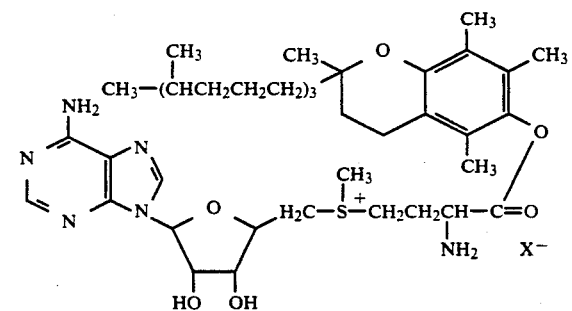

wherein X$^-$ is selected from the group consisting of iodide, chloride, bromide, hydroxyl, nitrite, phosphate and acetate. As indicated previously, a preferred compound is provided where X$^-$ comprises iodide, namely the compound α-(S-adenosylmethionine)-O-tocopherol.

The active agent is preferably administered by techniques well known in the pharmaceutical art, including those selected from the group consisting of intravenous injection, intramuscular injection, oral administration, topical administration, rectal administration, and inhalation.

The method of the invention also preferably employs a pharmaceutically acceptable carrier, such as one of the solid or liquid carriers described above. Moreover, the active agent is preferably administered in amounts of about 10 mg to about 1200 mg per kilogram of patient body weight per day.

According to another aspect of the present invention, a pharmaceutical composition for preventing the sickling of sickle cells in a patient having sickle cell disease is provided, which composition includes the novel compound of the invention; glutathione, or proteins or peptides containing glutathione; and at least one nutritional agent. This active agent system provides a synergistic effect that cannot be achieved by the individual administration of these agents.

Glutathione, $C_{10}H_{17}N_3O_6S$, is a well-known peptide that contains one amino-acid residue each of glutamic acid, cysteine, and glycine. The protein is believed to play an important role in biological oxidation-reduction processes, and as a coenzyme. Glutathione has been unexpectedly discovered to enhance the efficacy of the novel compounds provided by the invention, when employed with at least one nutritional agent. In addition, proteins or peptides containing glutathione have also been found to be effective in accordance with this aspect of the invention.

Nutritional agents which may be employed in accordance with the instant invention include those vitamins, minerals and the like well-known in the pharmaceutical art. Exemplary nutritional agents that may be utilized in the formulations of the invention, together with expected dosages for each nutritional agent, are set forth in Table 1 below.

TABLE 1

| Nutritional Agent | Expected Dosage |
|---|---|
| Vitamin A (Palmitate) | 10,000 I.U. |
| Vitamin D (Ergocalciferol) | 400 I.U. |
| Vitamin C (Ascorbic Acid) | 100 mg |
| Vitamin E (dl alpha tocopherol acetate) | 400 I.U. |
| Folic Acid | 400 mcg |
| $B_1$ (Thiamine Monoitrate) | 10 mg |
| $B_2$ (Riboflavin) | 10 mg |
| $B_6$ (Pyrodoxine HCl) | 3 mg |
| $B_{12}$ (Cyancobalamin) | 20 mg |
| Pantothenic Acid (d-calcium pentothenate) | 10 mg |
| Biotin | 10 mcg |
| Phosphatidyl Choline | 1,200 mg |
| Molybdenum ($Mo^{2+}$) | 500 mg |
| Selenium ($Se^{2-}$) | 50 mg |
| Potassium ($K^+$) | 99 mg |
| Iron (Ferrous Fumarate) ($Fe^{2+}$) | 36 mg |
| Magnesium (oxide) ($Mg^{2+}$) | 100 mg |
| Copper (Sulfate) ($Cu^{2+}$) | 2 mg |
| Zinc (Sulfate) ($Zn^{2+}$) | 15 mg |
| Manganese ($Mn^{2+}$) | 30 mg |
| Chromium ($Cr^{2+}$) | 100 mcg |
| Nickel ($Ni^{2+}$) | 20 mg |
| Calcium ($Ca^{2+}$) | 100 mg |
| Phosphorous ($P^{3-}$) | 80 mg |
| Iodine ($I^{1-}$) | 150 mcg |
| Cobalt ($Co^{2+}$) | 250 mcg |

Thus, the invention also provides a pharmaceutical composition which comprises a pharmaceutically acceptable carrier and an active agent system which comprises:

(a) from about 1% to about 98% by weight, based on the total weight of the pharmaceutical composition, of a compound having the formula:

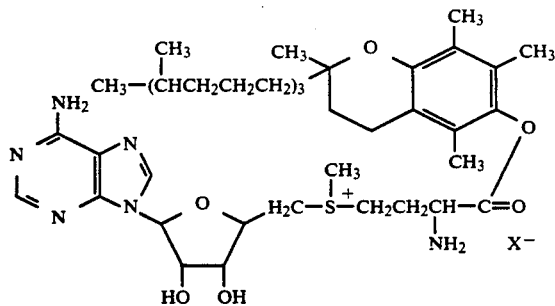

wherein $X^-$ is selected from the group consisting of iodide, chloride, bromide, hydroxyl, nitrite, phosphate and acetate;

(b) from about 1% to about 98% by weight, based on the total weight of the pharmaceutical composition, of glutathione, or proteins or peptides containing glutathione; and (c) from about 1% to about 98% by weight, based on the total weight of the pharmaceutical composition, of a nutritional agent selected from the group consisting of vitamin A, vitamin D, vitamin C, vitamin E, folic acid, vitamin $B_1$, vitamin $B_2$, vitamin $B_6$, vitamin $B_{12}$, pantothenic acid, biotin, phosphatidyl choline, molybdenum, selenium, potassium, iron, magnesium, copper, zinc, manganese, chromium, nickel, calcium, phosphorous, iodine, cobalt, and mixtures thereof.

This pharmaceutical composition may be administered in a therapeutically effective amount according to any of the techniques previously disclosed, including intravenous injection, intramuscular injection, oral administration, topical administration, rectal administration, and inhalation. Moreover, any of the pharmaceutically acceptable carriers described previously may be employed. In addition, the therapeutically effective amount of the active agent system will generally comprise from about 10 mg to about 1,200 mg of the active agent system per kilogram of patient body weight, and preferably about 10 mg to about 400 mg per kilogram body weight.

Without wishing to be bound by any particular theory, Applicant has characterized the method of treating sickle cell anemia provided by the present invention as an orthomolecular technique. In particular, it is believed that the active agents provided by the invention function to restore optimum amounts of substances that are normally present in the body, but which have been depleted in patients having sickle cell disease. Specifically, the pharmaceutical compositions of the invention are believed to assist in the stabilization of erythrocyte cell membranes by enhancing the useful energy that is available to the red blood cells of the patient. In this regard, the inventive method of treating sickle cell disease may be defined as a bioenergetic process. The pharmaceutical agents of the invention are believed to exhibit a therapeutic activity on the mitochondria, endoplasmic reticulum and similar cellular structures that provide useful energy to the sickle cell patient.

MITOCHONDRIA

The mitochondrion is a cellular organelle that is known to play a role in catabolism and ATP synthesis. Thus, the mitochondrion is often referred to as the cell's "powerhouse".

Mitochondria are the power producers of the cell because they extract energy from nutrients and oxygen, and provide this energy in a usable form to energize almost all cellular functions.

The mitochondrion is principally composed of two lipid bilayer-protein membranes which comprise an outer and inner membrane of the organelle. The inner cavity of the mitochondrion is filled with a gel matrix containing large amounts of dissolved enzymes that are necessary for extracting energy from nutrients. The inner membrane of the mitochondrion is folded into villi or crests. The outer membrane of the mitochondrion serves as a protective investiture of the cristae. Both inner and outer membranes of the mitochondrion have essentially the same molecular structure as the cell's plasma membrane.

Localized in the mitochondrion are the enzymes of the citric acid cycle and fatty acid oxidation; the electron-transport arrangements that deliver the electrons abstracted from intermediates of the citric acid cycle to oxygen; and the means by which the energy of this process is conserved by formation of ATP. Tracer studies with isotopes indicate that the heme portion of hemoglobin is synthesized mainly from acetic acid and glycine and that most of this synthesis occurs in the mitochondrion.

The mitochondrial phospholipids are mixtures of phosphatidylcholine, phosphatidylethanolamine, and cardiolipin. The fatty acids of mitochondrial phospholipids are generally highly unsaturated—a fact that accounts for the great susceptibility of the isolated mitochondrial system to lipid peroxidation.

ENDOPLASMIC RETICULUM

The endoplasmic reticulum is a continuous network of tubular and flat vesicular structures, constructed of lipid bilayer protein membranes. There are two types of interconnected endoplasmic reticulum depending on the presence of attached particles of ribonucleo protein, namely, smooth-surfaced and rough-surfaced reticulum.

Attached to the outer surfaces of many parts of the endoplasmic reticulum are large numbers of ribosomes composed mainly of ribonucleic acid, which function in the synthesis of protein in the cells. Part of the endoplasmic reticulum ribosomes are called the agranular or smooth endoplasmic reticulum. The agranular reticulum functions in the synthesis of lipid substances and in many other enzymatic processes of the cell.

The activity of the pharmaceutical compositions provided by the invention is believed to be related to ultrastructural changes in the mitochondria and endoplasmic reticulum which are stimulated by the disclosed active agents. The membranes of the mitochondria and endoplasmic reticulum are known to assume various functional states, i.e., linear or zig-zagging, collapsed or extended vesicle or tubule configurations, which correlate with biochemical activity or inactivity relating to the production of useful cellular energy. It is believed that the agents of the invention enhance the amount of useful cellular energy that is available to the sickle cell patient, thereby promoting stabilization of red blood cell membranes and minimizing the likelihood of erythrocyte sickling.

The following examples are given to illustrate the invention, but are not deemed to be limiting thereof. All percentages given throughout the specification are based on weight unless otherwise indicated.

EXAMPLE 1

Preparation of α-(S-adenosylmethionine)-O-tocopherol

The following example illustrates the preparation of the preferred active agent provided according to the present invention.

N-Acetyl-S-benzyl-L-homocysteine (0.5 g) was dissolved in 1,4-dioxane (25 ml). Dicyclohexylcarbodiimide (0.5 g) was added to the solution with stirring followed by the addition of α-tocopherol (1 g). The resulting reaction mixture was stirred at 30°-32° C. for eighteen (18) hours during which time a white precipitate separated. The mixture was then filtered and the filtrate evaporated to dryness in vacuo to give an oily residue.

The oily residue was added to dry ammonia (ca. 100 ml) which had been previously condensed in a 500 ml three-necked flask equipped with a stirrer and sodium hydroxide tube to maintain anhydrous conditions. While stirring, sodium was added to the reaction mixture in small pieces until the resulting blue color persisted for 5-10 minutes. 5'-O-p-Tolyl-sulfonyladenosine (0.5 g) was then added to the solution and stirring continued for ten (10) minutes. The ammonia was evaporated for three hours and the final traces thereof removed under diminished pressure, yielding a waxy solid residue. The residue was extracted with methylene chloride (2×25 ml) and the combined residue evaporated to dryness to give a waxy solid.

The waxy solid was dissolved in dimethyl sulfoxide (10 ml) containing acetic acid (3 ml) and the solution stirred with excess methyl iodide (1 ml) for 30 hours at 30°-32° C. The solvent was allowed to evaporate and the resulting residue was extracted with methylene chloride (25 ml) and dried with sodium sulfate. Evaporation of the solvent gave a clear oil which turned green when exposed to air.

The resulting compound, α-(S-adenosylmethionine)-O-tocopherol was recovered and stored for future use.

EXAMPLE 2

The compound prepared according to Example 1 was subjected to a toxicity study in accordance with techniques well-known in the art. The study was conducted on rats over a three-day testing period. The active agent was administered in dosages of 0.001%, and 0.01%, and 0.1%, based on the weight of the rat treated, on the first, second, and third days of the study, respectively. The results of the study, set forth in Tables 1-3 below, indicate that the active agent is substantially non-toxic in that none of the rats tested were killed after administration of the drug formulation.

TABLE 1

First day of study. 0.001% dosage of active agent.

| Rat No. | Weight (grams) After | Weight (grams) Before | Weight Change (grams) | Volume (ml) | Body Fluid Concentration 0.001% |
|---|---|---|---|---|---|
| #A | 27.3 | 27.2 | 0.1 | 0.07 | $7 \times 10^{-5}$ |
| #B | 26.2 | 26.1 | 0.1 | 0.07 | $7 \times 10^{-5}$ |
| #C | 28.8 | 28.7 | 0.1 | 0.07 | $7 \times 10^{-5}$ |
| #D | 25.0 | 25.0 | 0.0 | 0.0 | 0 |

TABLE 2

Second day of study. 0.01% dosage of active agent.

| Rat No. | Weight (grams) After | Weight (grams) Before | Weight Change (grams) | Body Fluid Concentraton 0.01% |
|---|---|---|---|---|
| #A | 28.5 | 28.3 | 0.2 | 0.14 |
| #B | 26.4 | 26.3 | 0.1 | 0.07 |
| #C | 29.5 | 29.4 | 0.1 | 0.07 |
| #D | 26.4 | 26.3 | 0.1 | 0.07 |

TABLE 3

Third day of study. 0.1% dosage of the active agent.

| Rat No. | Weight (grams) After | Weight (grams) Before | Weight Change (grams) | Volume (ml) | Body Fluid Concentration 0.1% |
|---|---|---|---|---|---|
| #A | 29.2 | 29.1 | 0.1 | 0.07 | $7 \times 10^{-2}$ |
| #B | 26.0 | 25.9 | 0.1 | 0.07 | $7 \times 10^{-2}$ |
| #C | 30.2 | 30.2 | 0.0 | 0.0 | 0 |
| #D | 25.4 | 25.4 | 0.0 | 0.0 | 0 |

The invention being thus described, it will be obvious that the same may be varied in many ways. Such variations are not to be regarded as a departure from the spirit and scope of the invention and all such modifications are intended to be included within the scope of the following claims.

What is claimed is:

1. A pharmaceutical composition for preventing the sickling of erythrocytes in a patient having sickle cell disease, the composition which comprises a pharmaceutically acceptable carrier and a therapeutically effective amount of from about 10 mg to about 1200 mg per kilogram of patient body weight of an active agent system which comprises:

(a) from about 1% to about 98% by weight, based on the total weight of said pharmaceutical composition, of a compound having the formula:

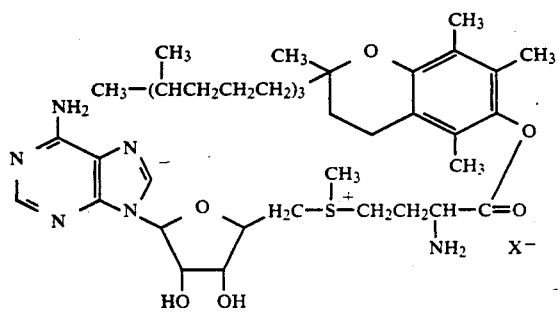

wherein $X^-$ is selected from the group consisting of iodide, bromide, hydroxyl, nitrite, phosphate and acetate;

(b) from about 1% to about 98% by weight, based on the total weight of said pharmaceutical composition, of glutathione, or proteins or peptides containing glutathione; and (c) from about 1% to about 98% by weight, based on the total weight of said pharmaceutical composition, of a nutritional agent selected from the group consisting of vitamin A, vitamin D, vitamin C, vitamin E, folic acid, vitamin $B_1$, vitamin $B_2$, vitamin $B_6$, vitamin $B_{12}$, pantothenic acid, biotin, phosphatidyl choline, molybdenum, selenium, potassium, iron, magnesium, copper, zinc, manganese, chromium, nickel, calcium, phosphorous, iodine, cobalt, and mixtures thereof.

2. A method for preventing the sickling of sickle cells in a patient having sickle cell disease, the method which comprises administering to said patient a therapeutically effective amount of a pharmaceutical composition which comprises a pharmaceutically acceptable carrier and from about 10 mg to about 1200 mg per kilogram of patient body weight of an active agent system which comprises:

(a) from about 1% to about 98% by weight, based on the total weight of the pharmaceutical composition, of a compound having the formula:

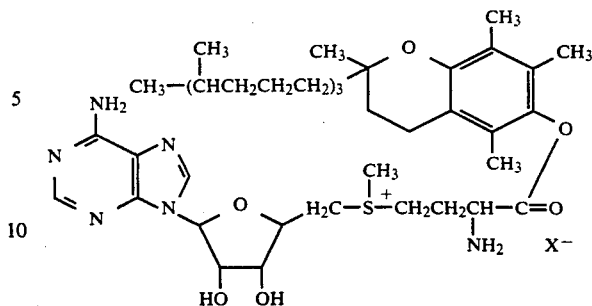

wherein $X^-$ is selected from the group consisting of iodide, bromide, hydroxyl, nitrite, phosphate and acetate;

(b) from about 1% to about 98% by weight, based on the total weight of the pharmaceutical composition, of glutathione, or proteins or peptides containing glutathione; and (c) from about 1% to about 98% by weight, based on the total weight of the pharmaceutical composition, of a nutritional agent selected from the group consisting of vitamin A, vitamin D, vitamin C, vitamin E, folic acid, vitamin $B_1$, vitamin $B_2$, vitamin $B_6$, vitamin $B_{12}$, pantothenic acid, biotin, phosphatidyl choline, molybdenum, selenium, potassium, iron, magnesium, copper, zinc, manganese, chromium, nickel, calcium, phosphorous, iodine, cobalt, and mixtures thereof.

3. The pharmaceutical composition of claim 1, wherein said pharmaceutically acceptable carrier is selected from the group consisting of solid form preparations and liquid form preparations.

4. The pharmaceutical composition of claim 3, wherein said solid form preparations are selected from the group consisting of powders, tablets, dispersible granules, capsules, cachets and suppositories.

5. The pharmaceutical composition of claim 3, wherein said liquid form preparations are selected from the group consisting of solutions, suspensions and emulsions.

6. The pharmaceutical composition of claim 1, further including one or more additional ingredients selected from the group consisting of diluents, flavoring agents, solubilizing agents, colorants, lubricants, suspending agents, binders, tablet disintegrating agents, stabilizers, buffers, sweeteners, dispersants, thickeners and mixtures thereof.

7. The pharmaceutical composition of claim 1, wherein $X^-$ comprises iodide.

8. The method of claim 2, wherein said compound is administered by a method selected from the group consisting of intravenous injection, intramuscular injection, oral administration, topical administration, rectal administration, and inhalation.

9. The method of claim 2, wherein said compound is administered in a pharmaceutically acceptable carrier selected from the group consisting of solid form preparations and liquid form preparations.

10. The method of claim 9, wherein said solid form preparations are selected from the group consisting of powders, tablets, dispersible granules, capsules, cachets and suppositories.

11. The method of claim 9, wherein said liquid form preparations are selected from the group consisting of solutions, suspensions and emulsions.

12. The method of claim 9, wherein said pharmaceutically acceptable carrier further includes one or more additional ingredients selected from the group consisting of diluents, flavoring agents, solubilizing agents, colorants, lubricants, suspending agents, binders, tablet disintegrating agents, stabilizers, buffers, sweeteners, dispersants, thickeners and mixtures thereof.

13. The method of claim 8, wherein $X^-$ comprises iodide.

* * * * *